United States Patent
Experton

(10) Patent No.: US 11,610,159 B2
(45) Date of Patent: *Mar. 21, 2023

(54) MOBILE DEVICE-BASED SYSTEM FOR AUTOMATED, REAL TIME HEALTH RECORD EXCHANGE

(71) Applicant: Humetrix, Del Mar, CA (US)

(72) Inventor: Bettina Experton, Del Mar, CA (US)

(73) Assignee: HUMETRIX, Del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/700,727

(22) Filed: Dec. 2, 2019

(65) Prior Publication Data

US 2020/0134517 A1 Apr. 30, 2020

Related U.S. Application Data

(63) Continuation of application No. 13/415,800, filed on Mar. 8, 2012, now Pat. No. 10,535,020.

(60) Provisional application No. 61/530,367, filed on Sep. 1, 2011, provisional application No. 61/475,199, filed on Apr. 13, 2011, provisional application No. 61/451,111, filed on Mar. 9, 2011.

(51) Int. Cl.
*G06Q 10/06* (2023.01)
*G16H 10/60* (2018.01)
*G16H 10/65* (2018.01)
*G16H 40/67* (2018.01)

(52) U.S. Cl.
CPC ............ *G06Q 10/06* (2013.01); *G16H 10/60* (2018.01); *G16H 10/65* (2018.01); *G16H 40/67* (2018.01)

(58) Field of Classification Search
CPC ........ G16H 10/60; G16H 40/67; H04L 41/22; A61B 5/0022; A61B 5/0077
See application file for complete search history.

(56) References Cited

U.S. PATENT DOCUMENTS

| 2002/0004832 A1* | 1/2002 | Yoon .................. H04L 63/0807 709/229 |
| 2003/0130867 A1 | 7/2003 | Coelho et al. |
| 2007/0125844 A1 | 6/2007 | Libin et al. |
| 2008/0172737 A1 | 7/2008 | Jinmei et al. |
| 2009/0058635 A1 | 3/2009 | Lalonde et al. |

(Continued)

FOREIGN PATENT DOCUMENTS

| WO | 2004102329 A2 | 11/2004 |
| WO | 2007/050877 A2 | 5/2007 |

OTHER PUBLICATIONS

Adams et al., "MeD-Lights," Proceedings of the ACM International Conference on Health Informatics, p. 800, New York, NY (Jan. 1, 2010).

*Primary Examiner* — Reginald R Reyes
(74) *Attorney, Agent, or Firm* — Loza & Loza, LLP; Anthony G. Smyth

(57) ABSTRACT

A method, an apparatus, and a computer program product for accessing electronic medical records are provided in which a portable computing device uniquely associated with a user authenticates an identification of the user and automatically retrieves information corresponding to the user from electronic healthcare records systems using the identification. The retrieved information may be combined with other information and electronically delivered to a healthcare provider.

25 Claims, 6 Drawing Sheets

(56) References Cited

U.S. PATENT DOCUMENTS

| | | | |
|---|---|---|---|
| 2009/0259493 A1* | 10/2009 | Venon | G16H 20/10 |
| | | | 705/3 |
| 2010/0115609 A1 | 5/2010 | Spence | |
| 2010/0241524 A1* | 9/2010 | Rogondino | G06Q 30/0601 |
| | | | 705/26.1 |
| 2011/0288874 A1* | 11/2011 | Hinkamp | G06F 21/6245 |
| | | | 705/1.1 |
| 2012/0232929 A1* | 9/2012 | Experton | G06Q 10/06 |
| | | | 705/3 |
| 2013/0331664 A1* | 12/2013 | Gilad-Gilor | A61B 5/741 |
| | | | 600/407 |

* cited by examiner

MOBILE DEVICE-BASED SYSTEM FOR AUTOMATED, REAL TIME HEALTH RECORD EXCHANGE

CROSS-REFERENCE TO RELATED APPLICATION(S)

This application is a continuation of U.S. patent application Ser. No. 13/415,800 filed on Mar. 8, 2012, and which claims the benefit of U.S. Provisional Application Ser. No. 61/530,367 filed on Sep. 1, 2011, of U.S. Provisional Application Ser. No. 61/475,199 filed on Apr. 13, 2011, and of U.S. Provisional Application Ser. No. 61/451,111 filed on Mar. 9, 2011, the contents of which applications are hereby incorporated by reference herein in their entirety.

BACKGROUND

Field

The present invention relates generally to electronic healthcare records and more particularly to access and exchange of electronic healthcare records using mobile computing devices.

Background

In today's healthcare environment individuals typically receive healthcare from multiple healthcare providers and often at multiple locations. Healthcare providers commonly lack accurate and up to date information regarding the care previously received by a patient from other providers. In order to deliver optimum, coordinated healthcare and most cost-effective healthcare to their patients, healthcare providers need to have ready access to an up to date medical history of their patients wherever they have received care, and the ability to exchange their most recent clinical findings and treatment plans to other healthcare providers who will be caring for their patients next.

To deliver such optimum care coordinated healthcare, new healthcare delivery and financing models have been defined, which emphasize coordination of care with the use of patient-centered medical homes (PCMHs) or accountable care organizations (ACOs). Implementation of such systems, however, can require significant changes in clinical practice and can result increased complexity in business, financing and contractual arrangements associated with the delivery and receipt of medical services. Healthcare information technology (HIT) systems are also now been developed and used to improve care coordination. HIT systems may include regional, federal and state health information exchanges (HIEs), provider-to-provider connectivity solutions using the nationwide health information network (NwHIN) and Direct protocol, or proprietary systems. However, such HIT solutions can be complex and costly to install and operate, and their use by providers (e.g. physicians) can be time-consuming and cumbersome, and often leave connectivity gaps between systems and providers.

SUMMARY

In an aspect of the disclosure, an electronic medical records access system comprises a portable computing device uniquely associated with one of a plurality of users. The portable computing device may be configured to execute an agent that authenticates an identification of the one user associated with the portable computing device. The portable computing device may be configured to execute an agent that automatically retrieves information corresponding to the one user from at least one electronic healthcare records system using the identification to access the at least one electronic healthcare records system. The portable computing device may be configured to execute an agent that electronically delivers a portion of the information to a healthcare provider.

The portable computing device may electronically deliver the portion of the information using a Bluetooth connection, a wireless network or by another method of communicating.

In an aspect of the disclosure, the portable computing device comprises one or more of a wireless telephone, a smart phone and a tablet computer. The portable computing device may retrieve the information from the at least one electronic healthcare records system using a cellular wireless telephone network. A portion of the information may be delivered to a computing device, such as a desktop or portable computing device operated by the healthcare provider. A portion of the information may be delivered using a server communicatively coupled to the portable computing devices associated with the one user and operated by the healthcare provider. A portion of the information may be encrypted.

In an aspect of the disclosure, the agent combines the retrieved information with other information retrieved from the at least one electronic healthcare records system to obtain combined information. Other information may comprise electronic health records of the user that are maintained by the portable computing device. The electronic health records maintained by the portable computing device may be encrypted using encryption keys uniquely associated with the one user.

In an aspect of the disclosure, a portion of the combined information or single health record delivered to the healthcare provider is selected based on consent of the record holder that may be expressly given or inferred from a request to transfer files to the provider, where the record holder has chosen to transfer these files. The consent may be based on an identification of the user. The identification of the user may be authenticated using a biometric measurement.

In an aspect of the disclosure, an electronic device comprising one or more processors and non-transient storage maintains data and instructions configured to cause one or more processors of a computing system to authenticate an identification of a user uniquely associated with the electronic device, automatically retrieve information corresponding to the user from at least one electronic healthcare records system using the identification to access the at least one electronic healthcare records system, and electronically deliver a portion of the information to a healthcare provider.

The electronic device may be adapted to be communicatively coupled to the computing system. A portion of the information may be delivered to a computing device operated by the healthcare provider. The computing device of the healthcare provider may be a portable computing device and may comprise one or more of a wireless telephone, a smart phone and a tablet computer. A portion of the information may be delivered using a server communicatively coupled to the portable computing device. A portion of the information may be encrypted.

In an aspect of the disclosure, retrieved information may be combined with other information retrieved from the at least one electronic healthcare records system to obtain a report or combined record. The other information retrieved from electronic healthcare records systems may comprise electronic health records of the user that are maintained by the portable computing device.

DETAILED DESCRIPTION

Figure 1:
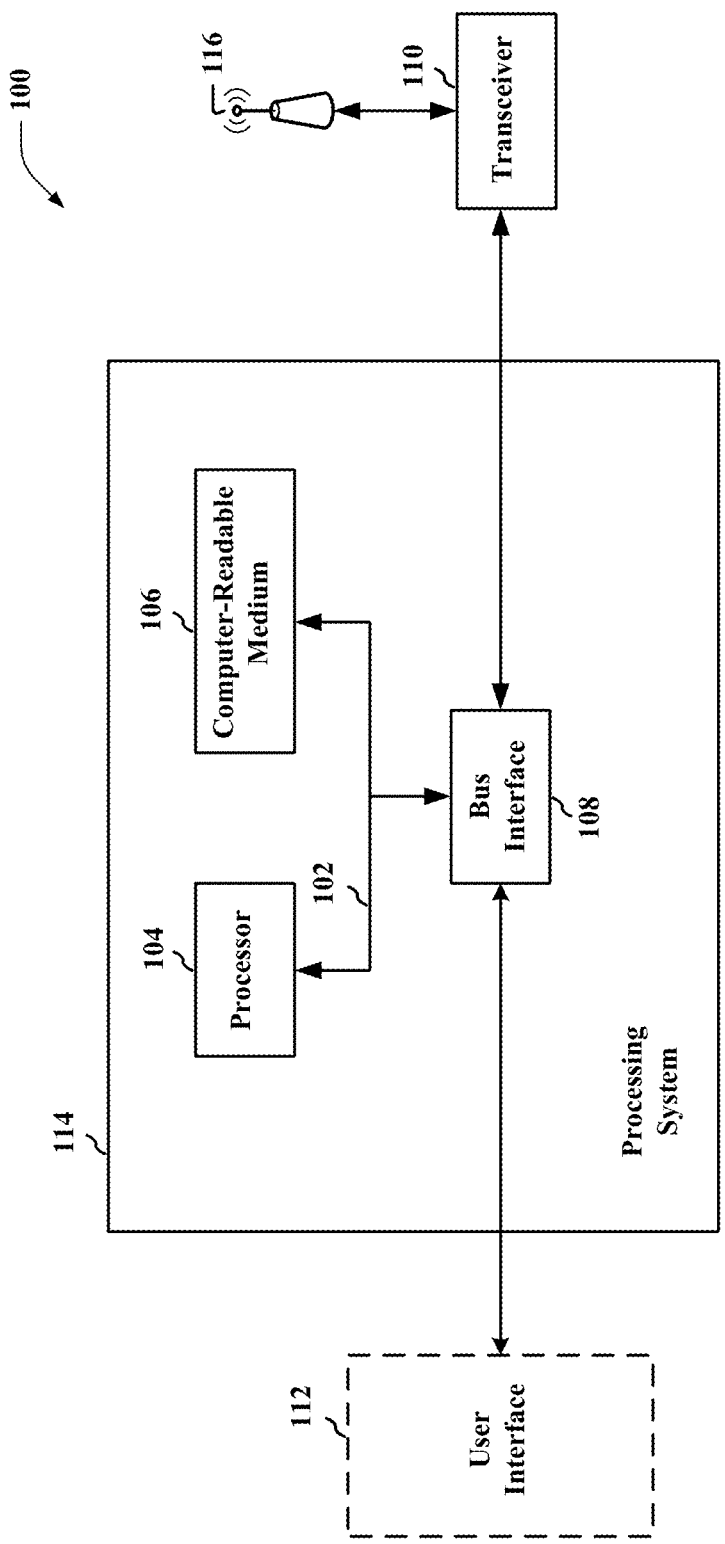
FIG. 1 is a diagram illustrating an example of a hardware implementation for an apparatus employing a processing system.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Several aspects of records management systems will now be presented with reference to various apparatus and methods. These apparatus and methods will be described in the following detailed description and illustrated in the accompanying drawing by various blocks, modules, components, circuits, steps, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

By way of example, an element, or any portion of an element, or any combination of elements may be implemented with a "processing system" that includes one or more processors. Examples of processors include microprocessors, microcontrollers, digital signal processors (DSPs), field programmable gate arrays (FPGAs), programmable logic devices (PLDs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise. The software may reside on a computer-readable medium. A computer-readable medium may include, by way of example, a magnetic storage device (e.g., hard disk, floppy disk, magnetic strip), an optical disk (e.g., compact disk (CD), digital versatile disk (DVD)), a smart card, a flash memory device (e.g., card, stick, key drive), Near Field Communications (NFC) token, random access memory (RAM), read only memory (ROM), programmable ROM (PROM), erasable PROM (EPROM), electrically erasable PROM (EEPROM), a register, a removable disk, a carrier wave, a transmission line, and any other suitable medium for storing or transmitting software. The computer-readable medium may be resident in the processing system, external to the processing system, or distributed across multiple entities including the processing system. Computer-readable medium may be embodied in a computer-program product. By way of example, a computer-program product may include a computer-readable medium in packaging materials. Those skilled in the art will recognize how best to implement the described functionality presented throughout this disclosure depending on the particular application and the overall design constraints imposed on the overall system.

FIG. 1 is a conceptual diagram illustrating an example of a hardware implementation for an apparatus 100 employing a processing system 114. In this example, the processing system 114 may be implemented with a bus architecture, represented generally by the bus 102. The bus 102 may include any number of interconnecting buses and bridges depending on the specific application of the processing system 114 and the overall design constraints. The bus 102 links together various circuits including one or more processors, represented generally by the processor 104, and computer-readable media, represented generally by the computer-readable medium 106. The bus 102 may also link various other circuits such as timing sources, peripherals, voltage regulators, and power management circuits, which are well known in the art, and therefore, will not be described any further. A bus interface 108 provides an interface between the bus 102 and a transceiver 110. The transceiver 110 provides a means for communicating with various other apparatus over a transmission medium. The transceiver 110 may provide a proprietary wired interface or a wired interface compliant or consistent with a standard such as universal serial bus (USB), FireWire, Ethernet, Serial Advanced Technology Attachment (SATA), etc. The transceiver 110 may provide a wireless interface and transmit and receive radio signals through an antenna 116, wherein a proprietary or standardized signaling protocol such as IEEE 802.11, WiFi, WiMax, CDMA, WCDMA, Bluetooth, etc. The transceiver 110 and antenna 116 may enable the device to communicate as a radio frequency identification device (RFID) device. The transceiver may enable optical, infrared and other communications. Depending upon the nature of the apparatus, a user interface 112 (e.g., keypad, display, speaker, microphone, joystick) may also be provided.

The processor 104 is responsible for managing the bus 102 and general processing, including the execution of software stored on the computer-readable medium 106. The software, when executed by the processor 104, causes the processing system 114 to perform the various functions described infra for any particular apparatus. The computer-readable medium 106 may also be used for storing data that is manipulated by the processor 104 when executing software.

The various concepts presented throughout this disclosure may be implemented using a broad variety of telecommunication systems, network architectures, and communication standards.

Various aspects of the present disclosure relate to an example involving electronic health records, although the various aspects of the invention may relate to the management and access of other types of records, including legal records, financial records, employment records, and so on. For example, certain aspects of the invention are applicable to point-of-sale authorization and identification of the parties to a transaction. In another example, certain aspects of the invention may enable secure transactions and exchange of information between clients and financial institutions.

Figure 2:
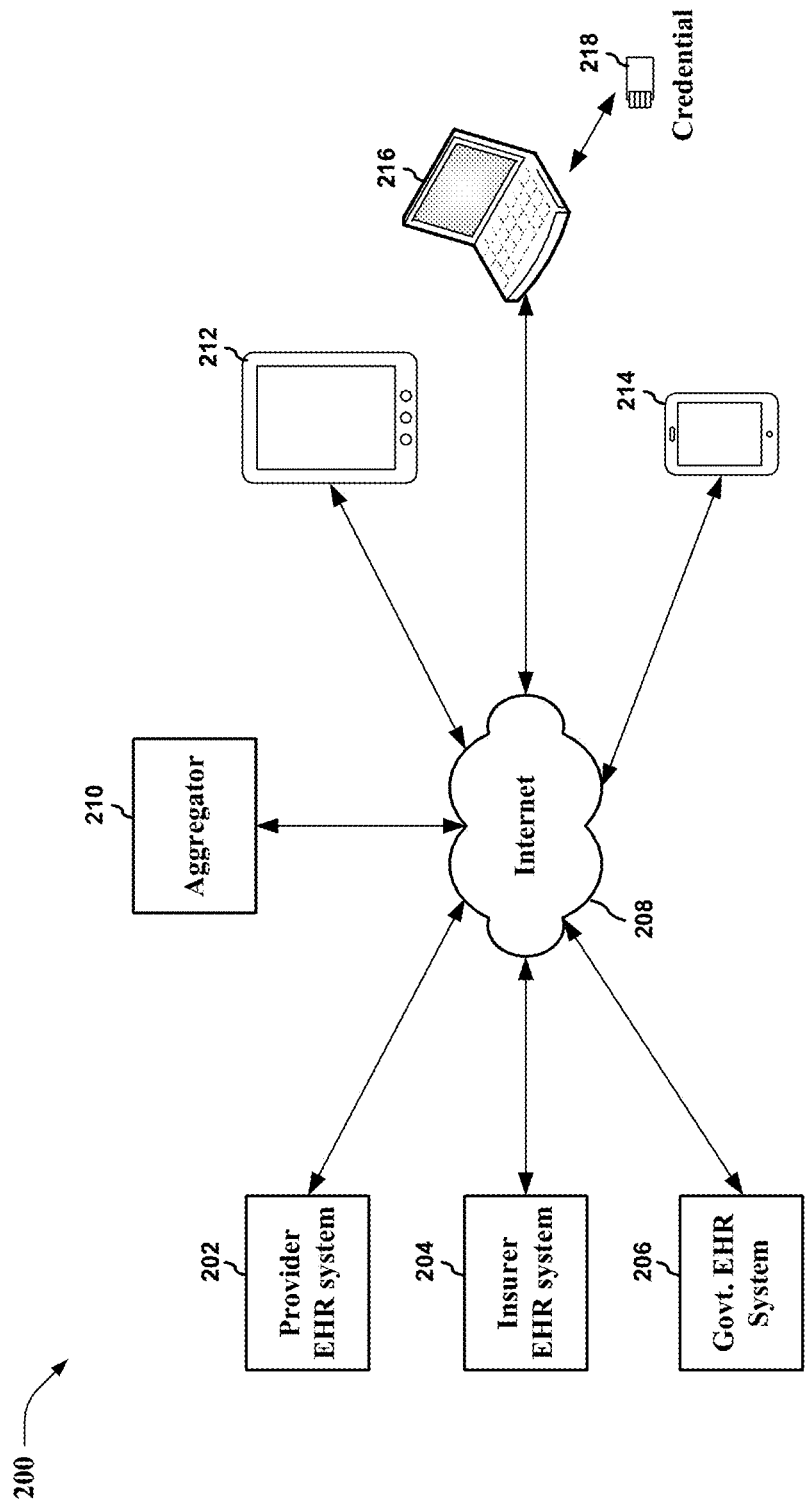
FIG. 2 is a block diagram illustrating an example of an electronic records delivery system according to certain aspects of the invention.

FIG. 2 illustrates a simplified example of a system 200 according to certain aspects of the invention. Electronic Health Records (EHRs) may be maintained in various locations and/or systems 202, 204, and 206. In the example, the EHRs are maintained by healthcare providers 202, or payors such as insurers 204 and government entities 206. Records maintained by EHR systems 202, 204, and 206 may include duplicate information maintained in two or more of systems 202, 204, and 206, although it is anticipated that at least some EHR information may be maintained in a single one of systems 202, 204, and 206.

A user may access records through a mobile device 212 or 214, such as a smart phone, a tablet computing device, a notebook computer, or other suitable mobile device. The user may be a service provider or an individual record owner who may be a patient of a provider system and/or an individual insured by an insurer, or an agent of the record owner. Typically, the record owner is a patient who receives healthcare services in multiple locations and/or from multiple healthcare providers. Healthcare providers may include one or more of a primary care provider (physician), a physician specialist, and a pharmacy. The patient may be insured by a private or public health insurance plan. Each of these different healthcare entities may maintain separate and distinct electronic health records for the patient.

The mobile device 212 or 214 may be adapted or configured, using an installed or downloaded application or agent to enable access to personal electronic health records that are maintained on one or more centralized databases 202, 204 and 206. The user may typically access electronic health records related to a transaction or the provision of healthcare services to a patient, and the records accessed may comprise personal health records, such as medical records and insurance records, which may be remotely located on centralized databases embodied in systems 202, 240, and 206 operated by a service provider, insurer or other entity.

In certain embodiments, EHR databases maintained on systems 202, 204, and 206 may accessed through a network 208. The network 208 may comprise one or more of a wireless network, a cellular access network, the Internet and/or a private network, etc. In certain embodiments, a record owner can access EHR databases individually to retrieve records related to a specific activity, service, and/or provider. In some embodiments, the record owner may identify a set of EHR databases to be accessed and combined, collated, or merged to obtain one or more of a combined record or combined report of EHRs. In some embodiments, the record user can specify a type of record to be accessed, regardless of which EHR databases maintain such records. In some embodiments, a record owner can generate a combined individual record for immediate access and use by the user, or for delivery to a healthcare provider such as a physician, typically on the healthcare provider's own computing system 212. The record owner may produce a combined record on-demand (on-the-fly), or may provide access to a combined individual record that is maintained by, or on behalf of the record owner and which is typically updated automatically and/or periodically. In some embodiments, the record owner may authorize and/or enable a provider to access records from a single EHR source, from multiple sources, and/or from an aggregator 210. In some embodiments, a record owner may authorize and/or enable a provider to access certain types of records, regardless of the location of those records.

As illustrated in FIG. 2, the individual records may be delivered to a physician's mobile computing device 212, such as a tablet computer or smart phone, although the combined individual record may also be delivered to a server or other computer of system 202, 204 and 206. In some embodiments, the record owner may cause a server or other network device 210 to deliver the combined individual record to system 202, 204, or 206 and/or to a physician's mobile computing device 212 or other computing device, such as a desktop computer. Aggregator 210 may be used to provide individual records when a record owner does not have access to a device 214 capable of producing and delivering the individual record or when the record owner's device 214 cannot connect to provider's computing device 212 or systems 202, 204, or 206.

Identification and authentication information may be maintained on record holder's device 214 to permit record owner to access each of systems 202, 204, and 206. The maintenance and control of the identification and authentication information by the records owner can reduce overall system complexity because a single command and identification process at device 214 can cause automatic access of relevant records on EHR systems 202, 204, 206 and/or from aggregator 210. For example, an agent installed on the record owner mobile device 214 may be configured to identify and authenticate the user of the device 214 through password, challenge, biometric scan and/or other means for authentication known in the art. Authentication may optionally be confirmed by a trusted third party device or service provider. Authentication information may be provided to each of systems 202, 204, and 206 and/or aggregator 210 to enable access to the EHR information related to the record owner.

The process of authentication and/or point of origin of the request may be recorded and may be used to prove consent of a record holder to a transfer of records to a provider. In some embodiments, a request from a user to transfer records may be considered to include consent of the record owner, based on prior identification and/or authentication of the identity of the user as the record holder. The record owner may be presented with a request to confirm transfer request. The request for confirmation may include a request for identification and/or a request to authenticate the identity of the recipient of the transfer request. In some embodiments, the user may configure the type of transfer to be performed for each request. For example, consent may be limited to a subset of the owner's EHR record. In some embodiments, the record owner may configure a default specification of the types of record that can be transferred to one or more service providers.

The user may authorize and/or initiate an access to electronic health records at a service provider facility. The user may prepare a combined EHR report or may store a set of EHR information from a variety of sources on a mobile device or on a storage device. Locally maintained information is typically encrypted. The record holder may transfer a portion or all of locally maintained information to a healthcare provider when seeking healthcare services. The user may also access certain records on-line from home to check on his insurance status, medical appointments, to see prescription refill status or to communicate by e-mail with his physicians.

Certain embodiments provide an interface to multiple electronic health records for both users and service providers. A user may provide authorization that enables a service provider to access some or all of the user's combined records. Thus, a provider may, at the user's discretion, access the user's individual EHRs maintained by a different provider at a different healthcare facility. In one example, a physician may directly, and easily, access all of the user records necessary to obtain a current view of the user's complete medical history, insurance eligibility status, and other information. Moreover, medical practitioners can directly access the user's records in order to update the user's health information.

When transferring records, the user identification may be authenticated using any combination of a user ID, password, challenge question and biometric information. Typically, the transfer is made contingent upon a two-way identification of a record holder and a healthcare provider. In-person identification may be made using direct sight. Additionally, both users' portable devices may establish a connection that is confirmed by both the record holder and the healthcare provider. In one example, the connection may comprise a session secured using encryption keys that are exchanged between the users. The encryption keys may be used to encrypt and decrypt information transmitted between the devices of the users. The transfer may be made only between proximately located devices. In one example, the record holder may initiate contact by selecting a physician's tablet computer from a list of devices within Bluetooth range, or within the same WiFi domain. The physician typically accepts the connection.

In certain embodiments, records may not be exchanged without a positive identification of the recipient. When the record holder and the healthcare provider are located in different physical locations, a location identification made by one or more of the record holder and the healthcare provider using one or more of a global positioning system and location information provided by a wireless network. For example, certain wireless network telecommunications services can provide accurate positional information based on triangulation and/or certain signaling characteristics of mobile devices. In some embodiments, an authentication or other service may be used to verify identity of, and subsequently connect a record holder and a healthcare provider when the parties are located different physical locations.

In certain embodiments, the user devices may be incompatible and may not be capable of direct connection. For example, and Android-based device may not be able to connect securely with a tablet computer based on a different operating system. When incompatible devices are used, a gateway may be used to facilitate the connection of the devices and may provide extended handshake services that identify both devices and establish a secure link between the devices. The gateway may be provided using a local or network server and/or a cloud service.

In certain embodiments, global positioning technology may be used to confirm proximity or specific locations of the record holder and provider devices. In some embodiments, cell technology, such as 4G LTE may provide location services to determine proximity or physical location information.

General purpose computing devices 216, such as a notebook or desktop computer, may also be used to access medical records, even where the computer 216 does not belong to the record owner. Record owner may provide an electronic credential 218 that, when read and used by computer 216, enables automatic access of combined individual records. Electronic credential 218 may comprise a hand-held device with a non-transitory memory and an embedded microprocessor or other programmable device. The electronic credentials may comprise a smart card, a USB flash drive, and radio-frequency identification (RFID) device, an NFC token, web-enabled phones, etc, and the credential may be embodied in an identification card or other format easily stored and secured by the user. In certain embodiments, access to the user's EHR information may be obtained by presenting the electronic credential 218 to a computing device 212 or 216, whereby the computing device can establish a wired or wireless connection with the electronic credential 218 that enables an exchange of data. The electronic credential 218 may comprise a small portable device issued by an insurer, a government agency, a primary healthcare provider system, etc. The electronic credential 218 may comprise a memory that maintains information including a personal identifier, a unique identifier assigned to the individual, an EHR locator address, login information, and/or other identifying information. The user may use the electronic credential 218 to access one or more EHR systems 202, 204, and 206 through a computing device 212 or 216, such as a personal computer (PC), tablet computer, smart phone or other suitably equipped processing device. In one example, the electronic credential 218 comprises a flash drive, a smart card, or a device that can connect wirelessly to the computing device 212 or 216. The user may present the electronic credential 218 to the computing device 212 or 216 in a manner appropriate to allow the electronic credential 218 to exchange information with the computing device 212 or 216, whereby the computing device 212 or 216 may automatically access and login to one or more EHR systems 202, 204, and 206 using the record owner's identification. The user may have access to the EHR systems 202, 204, and 206 for automated and simultaneous real-time access to medical records maintained therein. In one example, an agent or other application software embedded in the electronic credential 218, or accessed through a network 208 using information stored on the electronic credential 218, may be downloaded to the computing device 212 or 216 to enable harvesting of selected data from the different EHR systems 202, 204, and 206 and generate an on-the-fly summary record for a physician to view and use.

Certain embodiments enable automated access to multiple data sources. In one example, electronic credential 218 comprises an encrypted "electronic keychain" that may be maintained as a knowledge base that comprises identification and lists of sources of health related information for an individual. The knowledge base can include both the Internet address as well as identification and other credentials needed to enable access to the data. Typically, the health information is maintained by a plurality of healthcare providers or practitioners, and information may be accessible through repositories or databases, including insurance databases and healthcare record portals.

An electronic credential 218 may comprise a device that includes a combination of hardware and software that can encrypt and decrypt information stored on the electronic credential 218. The electronic credential 218 may be embodied in intelligent electronic devices (devices having at least a programmable controller), such as a universal serial device, a smart phone, a PC and a tablet computer. The electronic device may have sufficient processing capacity and storage to operate as a self-contained EHR access portal.

In certain embodiments, an on-the-fly summary of health information can be provided at a medical provider facility, for example. Information provided by an electronic keychain may be used to initiate access and retrieval of information from multiple EHR sources 202, 204, and 206. Information provided by the electronic keychain may include one or more agents or applications that may compile multiple electronic health records into a single summary form. The summary form may be provided in a standardized format, such as continuity of care record ("CCR"), a continuity of care document ("CCD"), and other suitable formats. In some embodiments, compiled health records may be presented in a consistent summary format regardless of the format used by the originating source. Accordingly, information provided or accessed through the electronic keychain may include templates and conversion modules that can be used to filter and reformat EHR information from a variety of sources 202, 204, and 206.

Figure 3:
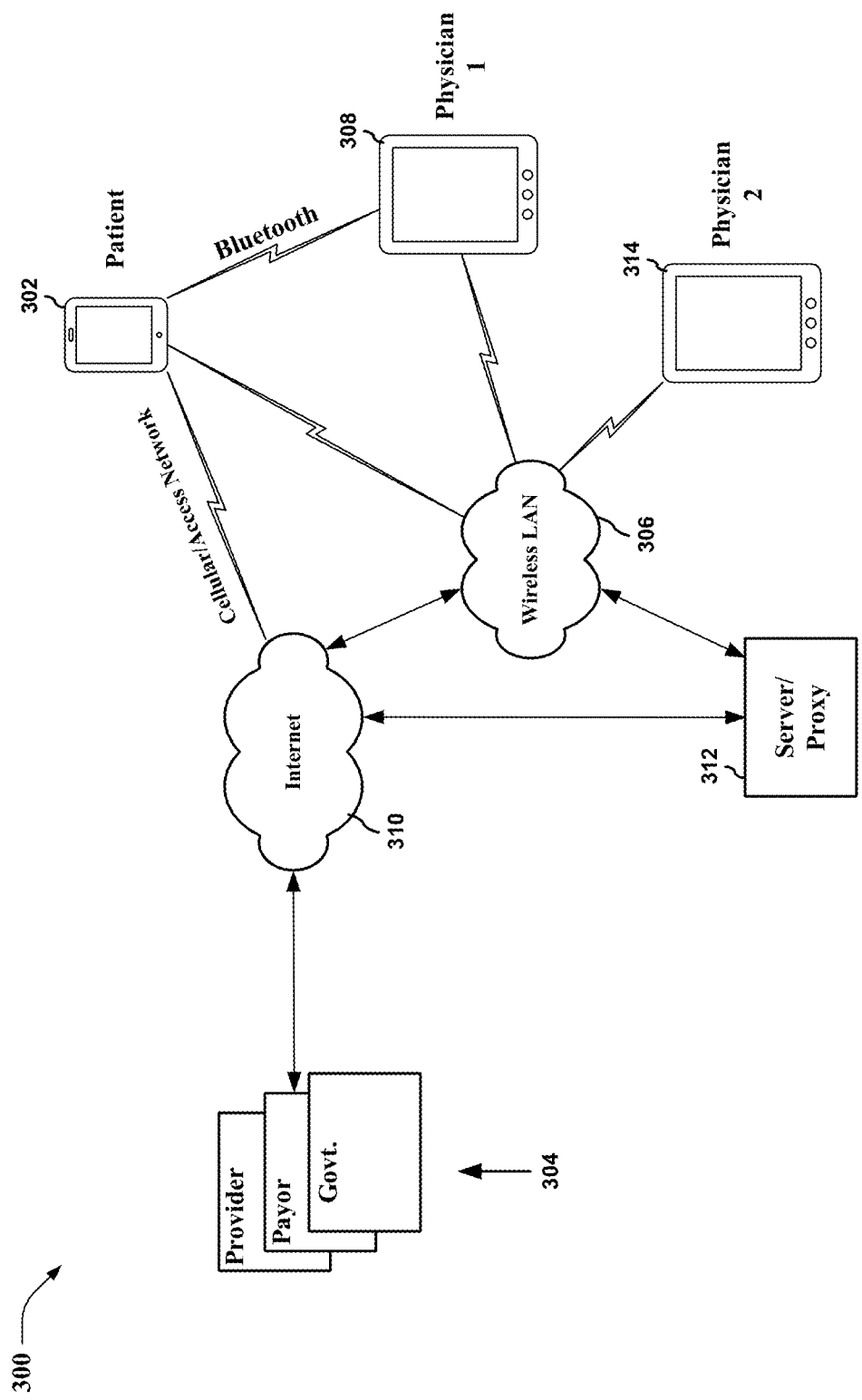
FIG. 3 is a conceptual diagram illustrating flow of electronic health records between a patient and physicians.

FIG. 3 is a block schematic 300 depicting data flow in transactions involving transfer of EHR records according to certain aspects of the invention. In a first scenario, a record owner may use a personal portable computing device 302 to directly transfer, or push, a combined record to a first provider device 308. For example, a patient visiting a physician's office may wish to provide updated records to the attending physician. The patient may initiate an agent or other application on a smart phone 302 to perform the transfer. The user may be required to provide identifying information, such as a username, a password, an answer to a challenge question and/or the user may be required to provide biometric information. The user may typically select which records should be provided to the physician.

Upon authentication, the agent may determine if a single or combined record is maintained on the patient device 302 and whether such record is current. The agent may request records from one or more healthcare providers, insurers, government agency, public payor or other source of EHR information (shown generally at 304). Having combined or updated the individual record or records, the agent may cause the patient device 302 to push a single record or combined records to the physician device 308 for immediate display. An application or agent on the physician device 308 may be manually initiated to receive the pushed information. In some embodiments, the physician device 308 may be adapted to respond to the push by opening an application or agent to receive or display the records upon receipt of a request for connection from patient device 302.

In certain embodiments, the physician may update records or retrieve other records on the physician device 308 and cause the updated or other records to be transmitted to the patient device 302. The patient device 302 may then provide the new or updated records to one or more of the EHR systems 304 or to another provider's computing device. In some embodiments, the physician may provide medical information to the patient device 302. For example, the physician may receive an X-Ray image on device 308 and may transfer the image to the patient device 302. In another example, the physician may cause device 308 to transmit information to the patient device that provides access to instructional or educational information to the patient device 302, including information on medications, dosage regimens and general information, such as educational information related to a medical condition.

User device 302 and physician device 308 may communicate using any available network or communication method, including WiFi, cellular communications, Bluetooth and other short range wireless communications. In certain embodiments, communication between devices 302 and 308 may be restricted to the use of short range communications methods to enhance security. For example, the use of a Bluetooth link between physician device 308 and patient device 302 may limit communications range to a single room, allowing both the physician and patient to verify that communication is properly established between devices 302 and 308 and the patient's privacy can be better protected. In certain embodiments, a patient may wish to transfer records to a physician who is not physically present using a wireless LAN 306 located in a medical facility and/or through the Internet 310 where the physician and patient are geographically remote from one another. In such cases, the patient and physician may establish a video conference connection to verify that verify that communication is properly established between devices 302 and 308.

In a second scenario depicted in FIG. 3, a server 312 may act as an intermediary or proxy between patient device 302 and a second physician device 314. As described for the first scenario, the patient may initiate a records transfer using device 312. In certain embodiments, intermediary 312 may provide one or more services, including user identification and authentication and record aggregation when patient device 302 is not configured or adaptable to perform such functions. For example, record owner may provide an electronic credential 218 (see FIG. 2) to a general purpose computing device 216, whereby the electronic credential 218 causes the computer 216 to transmit a request for service to the proxy 312. Proxy 312 may, for example, provide a web page to computer 216 which allows the patient to initiate a request that may be executed by proxy 312 on behalf of the patient.

In another example, patient device 302 and second physician 314 may be unable to directly communicate. Intermediary 312 may be configured to perform a gateway or routing function that permits exchange of information between 302 and 314 to communicate. Devices 302 and 314 may be unable to establish Bluetooth or WiFi connections with one another due to security settings of second physician device 314 and/or wireless LAN 306. In one example, intermediary 312 through a WiFi network may provide a gateway function when patient device 302 is connected to a different domain (guest domain), while the second physician device 314 is connected via a secured private domain of a local network 306.

In certain embodiments, proximity may be defined as closeness in both place and time. A proximity exchange may occur when real-time communication of health records and/or health information occurs between patient and physician devices 302 and 308 while the devices 302 and 308 are in physical proximity with each other and the users can identify each other by direct sight. In certain embodiments, proximity exchange may be used to communicate health records and/or health information from a first mobile device 302 to a second mobile device 308 over a local wireless network during a specific time period. The time period may be defined by a starting time when the communicating parties can identify each other by direct sight, either by physically seeing each other or by virtually viewing via video communication. Typically, the two people exchanging information will be together in the same room during the proximity exchange. As an example, a patient with a mobile phone 302 can send his health records to his doctor who is waiting with his tablet 308 in the same examining room. In another example, the doctor at the end of the visit can send to the patient some treatment instructions or literature related to his patient's diagnosis. In addition to having proximity of space (i.e. being in the same room) the patient and the doctor also have proximity of time. Each is expecting the communication to occur more or less immediately, for instance at the time when the physician is asking his patient about his medical history. In some embodiments, virtual identification can be made when the parties can see each other's face through video link. In some embodiments, devices 302, 308, and 314 may be adapted to perform facial recognition, iris scanning, fingerprint scanning or other biometric scanning when visual identification cannot be made by the parties. In some embodiments, visual recognition or a biometric alternative is required to permit access to the EHR information to be exchanged between the parties.

In some embodiments, standardized health summaries are made available to patients for easy download from government and private healthcare portals and to be shared with their healthcare providers. Certain embodiments of the invention enable immediate and/or proximate exchange of health records and related health information between a patient and a physician, or between two physicians, in a secure fashion in real time using mobile devices 302 and 308. Certain embodiments of the invention enable secure and easy communication of EHR data from one mobile device 302 to another mobile device 308 over a local wireless network during a patient encounter with implicit or explicit patient consent. The exchange may take place in a physician's office, in an emergency room, an urgent care center, or at a hospital without a need to configure network servers and provider workstations with individual account names, addresses and security login parameters. A proximity exchange provides immediate access and secure exchange of individual health information at the time when the sender and the receiver of the information being exchanged can physically recognize each other and are reachable to each other over a network such as a wireless network.

In certain embodiments, a physician can exchange health information with a patient or with another physician using mobile devices 302, 308 and 314. The exchange can occur between two mobile phones, two tablet or other computers, or between a mobile phone and a tablet or other computer.

Patient device 302 may be adapted using an application or agent that securely stores and organizes personal health records and health information. Patient device 302 may be adapted using an application or agent that automatically accesses a patient portal account and can automatically login to retrieve current and updated patient health records. Patient device 302 may be further adapted to automatically download and combine health records from patient web portals using login and other identification and authentication maintained by the patient device 302.

In certain embodiments, patient device 302 may be adapted to capture photographs of health documents and/or body parts using a camera in the mobile device 302. Patient device 302 may be adapted using an application or agent that accesses records created by other applications on the patient's mobile device. Proximity exchange may be used to transfer one or more health records and health information to a physician.

Patient device 302 may be adapted using an application or agent that directly receives health records, such as a visit summary, a referral note, test results, patient instructions, etc., from a physician using proximity exchange from the physician's mobile device 308.

Patient device 302 may be adapted using an application or agent that enables receipt of different types of records, including documents, photographs, audio and/or video recordings that may transferred by a physician using proximity exchange from the physician's mobile device 308 and the device 302 may be further configured to store and organize records exchanged to and from different physicians.

Physician device 308 may be adapted using an application or agent that can securely store and organize individual patient records and health information associated with several patients. Physician device 308 may be adapted using an application or agent that accesses records created by other applications, such as an electronic medical record (EMR) application, on the physician's mobile device 308.

Physician device 308 may be adapted using an application or agent that takes photographs of patient records and/or patient body parts using a camera of the mobile device 308. Physician device 308 may be further adapted to create an audio recording, including follow-up care instructions, and to store such recordings as part of the patient's record on the physician's mobile device 308.

Physician device 308 may be adapted using an application or agent that directly receives health records from a patient, using proximity exchange from the patient's mobile device and that downloads health related information from a variety of provider, electronic medical record, health information exchange and other portals.

In some embodiments, either the patient or the doctor can initiate a proximity exchange. The initiator of the communication may push a button or otherwise activate a function of an agent or application of their mobile device 302 or 308. The initiator device 302 or 308 may then broadcast over the wireless network an identification that may include a name that the other party can positively identify. The recipient may be notified that a request for proximity exchange has been received and may receive the name or names of the initiator. The recipient may choose between initiators detected within range of the recipient's mobile device 302 or 308 (e.g. a different physician and a different patient may be initiating an exchange in a nearby examining room). The proximity exchange may be authorized to commence when the recipient accepts the initiator.

In one example, Bluetooth and WiFi networks may be present. A mobile device may first attempt to advertise its desire to perform a proximity exchange using a WiFi Access Point (AP) if it is able to gain access to one within its wireless range. If the devices of both communication parties are able to access the same AP at the same time then the proximity exchange is performed through the AP, otherwise an attempt is made to connect them over Bluetooth. In some embodiments, Bluetooth connections are attempted first.

In certain embodiments, data is encrypted for transfer by proximity exchange. Encryption provides security that is not dependent upon on the security features of the underlying wireless network. Patient data such as health records and personal health information may be stored in encrypted form in mobile devices 302 and 308. In one example, encryption is performed using AES encryption algorithms with a secret encryption key that may be unique for the device 302 or 308. The encryption keys may be generated during configuration and installation of the agent or application on the device 302 or 308. Encryption keys may be based on a user password and a 64 byte random number. Encryption keys may be securely stored on the device in special secured hardware. This encryption protects both the confidentiality and the integrity of the data on the mobile devices 302 and 308.

Prior to transmission by proximity exchange, encrypted data may be first decrypted using the local cryptographic key of the sending device. The decrypted data may then be encrypted using a cryptographic key, known to both sender, and receiver and that is created dynamically to exist only during the lifetime of the communication session. The Diffie-Hellman algorithm may be used to create a communication session cryptographic key in such a way that only the two mobile devices 302 and 308 know the key. When encrypted data is received at the destination device 308 or 302, it can be decrypted using the key associated with current proximity exchange and then re-encrypted using the local cryptographic key of the destination device before it is stored.

In certain embodiments, health records and related health information can be securely exchanged in real-time without the need for predefined network infrastructure. Proximity exchange may provide secure communication between two parties who can physically recognize each other and can communicate electronically with each other over a network.

In certain embodiments, personal identification and contact information can be exchanged between patient device 302 and physician device 3080 as an option during proximity exchange. Personal identification information can include name, phone number, e-mail address, photograph, and such information may facilitate later contacts between the doctor and patient. In some embodiments, the contact information is exchanged automatically, without the requirement for each party to request it to be sent. Contact information may be automatically attached to records exchanged between the parties to enable easier filing and to enable accelerated retrieval on the respective devices 302 and 304.

Figure 4:
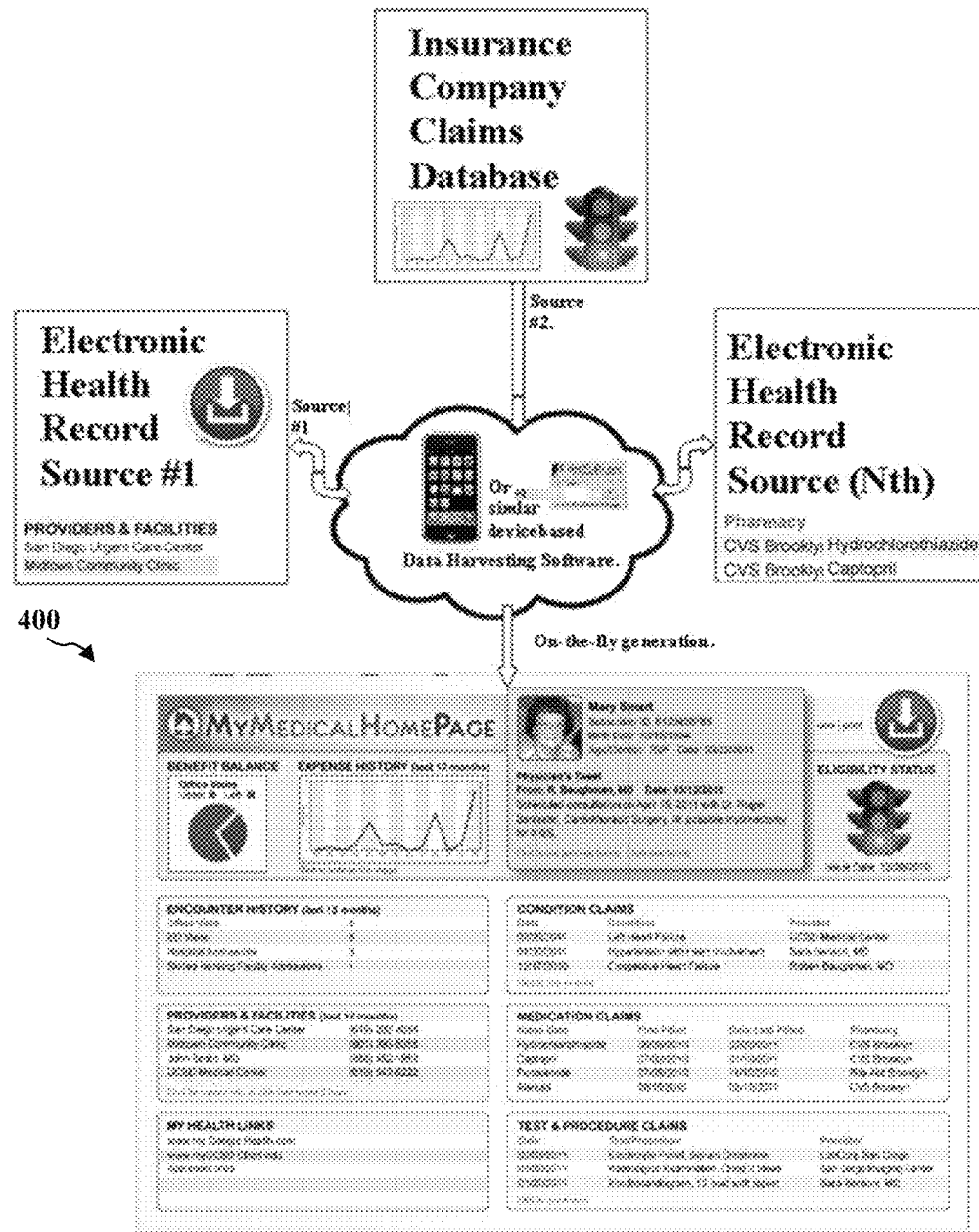
FIG. 4 illustrates a view of medical records provided to users of systems deployed according to certain aspects of the invention.

Record owners and providers may access the record owner EHR through a personalized portal provided on a mobile device or a conventional computing platform. Record owners may access their EHR information from a plurality of different sources and may provide one or more providers with partial or complete access to their EHR information. FIG. 4 illustrates a presentation of EHR information using a personalized portal according to certain aspects of the invention. The personalized portal may present a single display area that includes information from a plurality of sources including healthcare practitioners, insurance companies, an entity responsible for payment for services and other providers. EHR information may be combined remotely using a computer system or network server to access a plurality of EHR systems, before filtering and presenting the information to the record owner or provider. An aggregation server may reduce system complexity by providing identification, authentication, and qualification services related to the record owner and provider base as a centralized service, rather than requiring the plurality of EHR systems to maintain authentication information for the record owner and provider base. In some embodiments, a portal or agent may directly access and combine EHR information from the plurality of EHR systems.

Qualification services may filter results obtained from the plurality of EHR systems. Records received may be filtered based on certain predefined rules which may enforce government regulations. For example, certain records may not be accessible if access would cause healthcare information to be transferred between state or national jurisdictions. Records received may be filtered based on rules established by the record owner, a provider or the EHR system supplying the records. In one example, a record owner may determine a set of EHR records or a class of EHR records that should be withheld from one or more provider. The record owner may request that EHR records sent to a podiatrist should not include records related to psychiatric treatment, and vice versa.

An aggregator may format the information for display and/or may provide the information to an interface application that delivers a final format for display to the physician or other user. Interface application may be embodied in a portal or agent deployed on a record owner's computing device. Interface application may be provided as a plug-in on a network application at a provider location. Information provided by aggregator may be displayed in a web browser, a custom viewer application or in any suitable office automation application, such as a document reader or presentation tool. In certain embodiments, the display format may be specified and/or customized based on some combination of preferences and requirements of an end-user, a system administrator, a provider, payer and the record owner whose records are to be displayed. For example, the record owner may determine which fields are to be displayed and which data should be withheld. In another example, financial information is selected for display based on authorization levels set for the end-user.

In a certain embodiments, the record owner is a patient who receives, or expects to receive, healthcare services in a plurality of locations from multiple healthcare providers, such as his primary care provider (physician), a physician specialist and a pharmacy. The record owner may be insured by a private or public health insurance plan. Each provider may maintain separate and distinct electronic health records for the record owner. In some embodiments, record owner is permitted access to at least a portion of the records maintained by a provider on-line when such access is for the use of the record owner. For example, a record owner may access certain records from home to check on his insurance status, medical appointments, to view prescription refills, or communicate by e-mail with attending physicians.

Certain embodiments provide a record owner-controlled, practical, flexible, direct access to the record owner's health record that is continuously available. In some embodiments, the record owner may print and/or store a summary of online records on a removable storage device when it is necessary to present EHR records to one or more providers who are not users of the electronic delivery systems described herein. It will be appreciated however, that the printed or stored records are typically static and, if not updated in a timely manner, can become outdated by the time the records are presented at the point of care. Furthermore, the saved or printed record will typically not be available at all times, including during an emergency or at the time of a routine healthcare appointment, and may not be securely stored or carried; accordingly, these stored or printed records can be subject to loss or tampering. Electronic access to EHR records may additionally resolve existing complex and ineffective patient consent management solutions, typically paper-based and single facility-based.

Consent may be provided by record owners as part of a request to deliver the record owner's EHR records. Certain embodiments provide direct access by healthcare providers to record owner records, whereby current record owner records are directly downloaded to the provider's system. The record owner may be required to provide authentication when requesting that a portion or all of the record owner's records are directly pushed to a provider system. In some embodiments, the record owner may also provide time-limited consent to permit a provider to request and access patient records directly from another service provider or from an aggregator. Consent may be provided directly by the record owner using a portal or agent, which may be implemented in a smart phone or other portable processing device.

A portal or agent may be provided on a computing device. A portal may provide access to a record owner's EHR information through a browser or an application or agent that resides temporarily on the computing device. The portal may comprise an application that is downloaded and executed through a browser or loaded from a portable storage device, such as a USB drive. In one example, a USB drive may be used as a credential to identify and/or authenticate a user of the USB drive, through encryption keys, biometric information, etc., and may provide an application that enables the record owner to establish a portal on the computing device. The USB drive or another credential may be issued by his insurer, the government, or his primary healthcare provider system, etc., and may maintain record owner information such as a personal and unique identifier assigned to the record owner, a record locator address and login. The USB drive may also be configured to maintain a previously downloaded EHR document, typically in encrypted form.

The portal may comprise one or more downloadable applications and may deliver services performed by a network server. An agent may be installed or otherwise maintained by a computing device. The agent typically performs one or more functions that allow a record owner to access EHR information. The agent may identify a wireless device such as an RFID, a Bluetooth-enabled device, a WiFi connected device or another device that can be used to identify the user. The agent may be an application installed on a smart phone, tablet computer or notebook computer, whereby the record owner may use an identifier to gain access to EHR information. Identification may comprise a combination of user ID, password, challenge, biometric information such as a fingerprint, iris scan, facial scan effected by an on-board camera, and so on.

The agent or portal may be configured to perform a plurality of functions including record owner identification and authentication, access to EHR records, identification and authorization of EHR records to be pushed to a provider, aggregation of EHR records and direct push of EHR records from the record owner's personal portal to a provider's system.

In certain embodiments, a record owner may use a smart portable device that has a processor and storage. The record owner may connect a flash drive, smart card, a wirelessly connectable storage device, or the like to the computer. In one example, the record owner may present a Near Field Communication (NFC) device, such as an RFID or smart phone that responds to or activates an NFC receiver on a provider computing workstation. The record owner may also use an optical reader to capture a barcode, or biometric information that automatically enables access to the EHR information. Additionally, a device to device communication protocol between the patient's device and a provider's portable device may be employed to automatically access and exchange electronic, or initiate such exchange, with the healthcare provider.

An example of a summary form 400 is shown in FIG. 4. The summary form may be tailored to the requirements of the user, whether an EHR holder, an insurance provider, a government agency, a physician or other healthcare provider. The summary form may be formatted for ease of viewing on any suitable platform. The summary form may be presented in a single view, window and/or screen to allow a physician to access desired information in one place, with a minimum of required navigation. This single screen display can be generated on the fly and can include clinical information (e.g. in CCD/CCR format), administrative information and financial information, such as insurance eligibility information and past utilization and encounter information. The healthcare provider can typically obtain immediate access to the type, amount and location of services received by a patient, as well as out of pocket expenses incurred.

Figure 5:
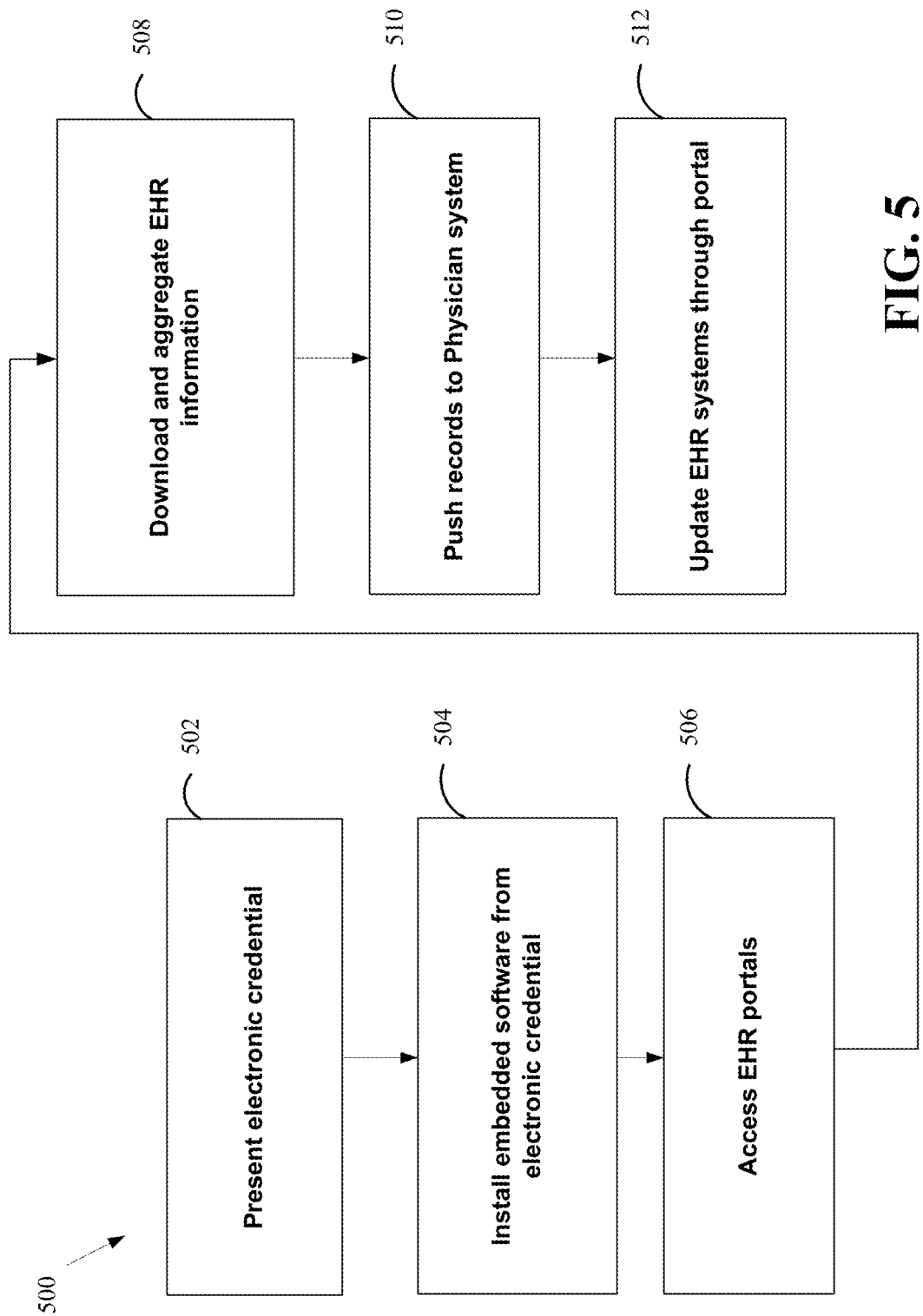
FIG. 5 is a flow chart of a method of health record exchange.

With reference to FIG. 5 and FIG. 2, a process according to certain aspects of the invention will be described. For the purposes of the description, an example an embodiment of the invention used by military Veterans will be described, whereby a typical Veteran accesses healthcare at different Veterans Administration (VA) and non-VA provider sites and EHR information for the Veteran is maintained by government and non-government entities. In the example, an exchange can occur between points of care, whereby electronic health records can be automatically downloaded from various patient portals by a Veteran's portable computing device 214 or electronic credential 218, which has been adapted through the installation of an embedded application. Various patient portals may be accessed through device 214 or 218, including My HealtheVet at the VA, TRICARE Online, and MyMedicare.gov and other examples.

Figure 6:
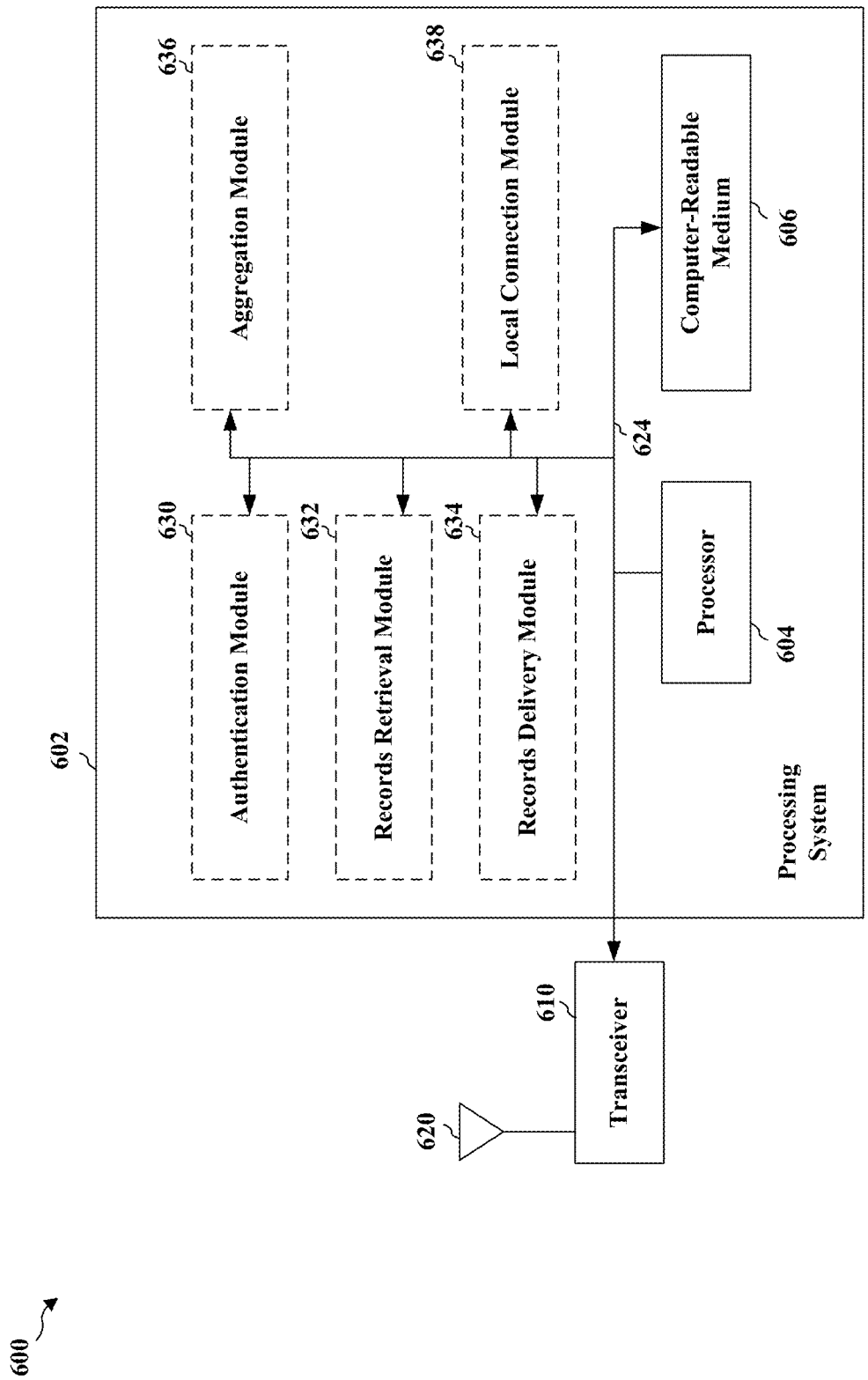
FIG. 6 is a diagram illustrating an example of a hardware implementation for an apparatus employing a processing system according to certain aspects of the invention.

With regard to the flowchart 500 of FIG. 6, at step 502 Veteran patient may present an ID card 218 that comprises a USB flash drive. The ID card may enable automatic communication/exchange of online health records with a provider EHR system 202. At step 504, software embedded in the Veteran's card 218 is automatically loaded and executed upon insertion and/or detection by an Internet-ready computing device 216. Typically, no software or system integration is required and the software may directly launch a login screen for entry of the Veteran's single chosen password in order to grant the provider consent of the patient to proceed.

At step 506, the device embedded software may then auto launch and automatically login into one or more of the Veteran's selected EHR enabled patient portals. The computing device 216 may then download and combine EHR records, automatically and as directed by the device embedded software. The device embedded software may additionally reformat the downloaded EHR information into a clinically prioritized format in a single view (see 402). This single view may also include a reply prompt window for the provider to send, at step 610, a follow up note, with or without attachments, to the Veteran's primary care or referring physician. The follow up note may be transmitted by secure Email, Fax and/or secure messaging.

As shown in FIG. 2, a Veteran's mobile device 214 may comprise a smart phone or tablet computer on which an application or agent has been installed or embedded, thereby obviating the need to perform steps 502 or 504. Moreover, the application or agent may adapt the Veteran's device 214 to maintain at least a summary report of EHR records. The application or agent may also adapt the Veteran's device 214 to automatically access one or more EHR portals (step 506) and download and combine EHR records from the portals (step 508). Typically, at step 510, records can be pushed to the physician device 212 upon consent and authentication of the Veteran. The records may be pushed to a provider device 212 using, for example, a service discovery protocol. An application or agent on the provider device 212 may signal its presence, which enables the Veteran to execute a transfer of records by commanding device 214 to directly push selected records to the provider's device 212. The provider may be prompted to choose whether or not to accept the Veteran's records before or after transmission of the records by the Veteran's device 214.

The physician may optionally provide updates records to Veteran's device 212, 214 or 218 which may then be relayed to the EHR systems 202, 204, or 206 through one or more portals. Typically, the provider reviews the received records and is provided a reply prompt to send information to the Veteran's device 214. For example, the information sent by the physician may include a follow up note to the Veteran's primary care or referring physician. Optionally information such as a follow-up note may be transmitted by secure Email, Fax and/or secure messaging.

FIG. 6 is a conceptual block diagram 600 illustrating the functionality of an exemplary apparatus 602 as used in a provider location for accessing medical records. The apparatus 600 may be a portable or non-portable computing device, having a processor 604 and non-transitory storage 606 in which an agent or software may be installed that includes one or more modules 630, 632, 634, 636 and 638.

Apparatus 600 may include an authentication module 630 identifies and/or authenticates the user associated with the apparatus 600. Module 630 may identify the user using a biometric measurement, a password, user identifier, RFID device and/or a challenge.

Apparatus 600 may include a records retrieval module 632 that automatically retrieves information corresponding to the one user from at least one electronic healthcare records system using the identification to access the at least one electronic healthcare records system. Apparatus 600 may retrieve the information from the at least one electronic healthcare records system using a cellular wireless telephone network.

Apparatus 600 may include a records delivery module 634 that electronically delivers a portion of the information to a healthcare provider. The apparatus may deliver the information using transceiver 610 and antenna 620, which may be configured to support Bluetooth communications and/or communications through a wireless network, such as a WLAN or cellular network. Accordingly, apparatus 600 may comprise one or more of a wireless telephone, a smart phone and a tablet computer. A portion of the information may be delivered to a different computing device operated by the healthcare provider. A portion of the information is delivered using a server communicatively coupled to the portable computing devices associated with the one user and operated by the healthcare provider. A portion of the information may be encrypted.

Apparatus 600 may include a local connection module 638 that establishes a data and/or audio-visual link with a provider. The apparatus may establish a connection using transceiver 610 and antenna 620, which may be configured to support Bluetooth communications and/or communications through a wireless network, such as a WLAN or cellular network. Accordingly, apparatus 600 may comprise one or more of a wireless telephone, a smart phone and a tablet computer. Module 638 may perform other functions, including automatically providing consent to allow providers to download records or the user.

Apparatus 600 may include an aggregation module 636 that combines the retrieved information with other information retrieved from the at least one electronic healthcare records system to obtain combined information. The other information may comprise electronic health records of the user that are maintained by apparatus 600. Electronic health records maintained by the apparatus may be encrypted using encryption keys uniquely associated with the one user.

One or more of modules 630, 632, 634, 636 and 638 may combine to perform a method comprising the steps of receiving from a first portable computing device, information identifying a user of the first portable computing device and a request for selected healthcare records corresponding to the user and an identity of a healthcare provider, causing the first portable computing device to authenticate identity of the user, wherein the authentication of the identity of the user serves as a consent of the user to release the selected healthcare records, and upon receiving information confirming the authentication of the identity of the user, transferring the selected healthcare records to a second computing device operated by the healthcare provider. In some embodiments the portable computing device maintains encrypted information that identifies the user.

The method may further comprise updating at least a portion of the selected healthcare records using information received from the healthcare provider. The method may further comprise healthcare records other than the selected healthcare records using information received from the healthcare provider. The method may further comprise creating new healthcare records using information received from the healthcare provider.

In some embodiments, the selected healthcare records comprise records from a plurality of sources, including at least one provider source and a payer source. In some embodiments, transferring the selected healthcare records includes receiving an acceptance from the healthcare provider. In some embodiments, the user and the healthcare provider are located in close proximity and wherein the transferring the selected healthcare records is contingent on a direct visual identification made by one or more of the user and the healthcare provider. In some embodiments, the user and the healthcare provider are located in different rooms and wherein the transferring the selected healthcare records is contingent on a virtual visual identification made by one or more of the user and the healthcare provider.

It is understood that the specific order or hierarchy of steps in the processes disclosed is an illustration of exemplary approaches. Based upon design preferences, it is understood that the specific order or hierarchy of steps in the processes may be rearranged. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The invention claimed is:

1. A portable computing device configured to control exchanges of health-related information, comprising:
   an electronic credential that uniquely associates a portable computing device with an individual who owns health-related information stored in the portable computing device; and
   a processor configured to:
      use the electronic credential to authenticate a user of the portable computing device as the individual who owns the health-related information;
      receive a transfer request from the authenticated user that includes a time-limited consent to release a selected portion of the health-related information to a proximately located device;
      use the electronic credential to access the health-related information;
      establish wireless communication between the portable computing device and the proximately located device; and
      cause the portion of the health-related information to be wirelessly transmitted to the proximately located device responsive to the request received from the authenticated user and in accordance with the time-limited consent,
   wherein the portion of the health-related information is selected for transfer to the proximately located device using a filter that is based on rules established on the portable computing device by the authenticated user.

2. The portable computing device of claim 1, wherein the processor is configured to:
   establish a connection through a wireless network with a plurality of electronic health records systems (EHR systems); and
   use the time-limited consent to update the health-related information that is stored in the portable computing device or in one or more of the plurality of EHR systems.

3. The portable computing device of claim 1, wherein the processor is configured to:
   establish a connection through a wireless network with a repository of electronic health records; and
   use the time-limited consent to update the repository using the health-related stored in the portable computing device.

4. The portable computing device of claim 3, wherein the repository comprises a payor or electronic healthcare records system.

5. The portable computing device of claim 3, wherein the processor is configured to:
   create new healthcare records in a set of electronic healthcare records stored in the portable computing device; and
   use the time-limited consent to provide the new healthcare records to the repository.

6. The portable computing device of claim 5, wherein the processor is configured to create the new healthcare records by accessing records created by one or more applications executed on the portable computing device.

7. The portable computing device of claim 5, wherein the processor is configured to create the new healthcare records after receiving modified electronic healthcare records from a healthcare provider.

8. The portable computing device of claim 1, wherein the processor is configured to:
   receive modified electronic healthcare records; and
   transmit the modified electronic healthcare records to a healthcare provider.

9. The portable computing device of claim 8, wherein the modified electronic healthcare records include new healthcare records created by one or more applications executed on the portable computing device.

10. The portable computing device of claim 1, wherein the portable computing device comprises a smart phone.

11. The portable computing device of claim 1, wherein the portable computing device comprises a tablet computer.

12. The portable computing device of claim 8, wherein the processor is configured to:
   cause the modified electronic healthcare records to be delivered to a computing device operated by the healthcare provider.

13. A method for controlling exchanges of health-related information, comprising:
   using an electronic credential maintained in a portable computing device to authenticate a user of the portable computing device as an individual who owns health-related information stored in the portable computing device;
   receiving a transfer request from the authenticated user that includes a time-limited consent to release a selected portion of the health-related information to a proximately located device;
   using the electronic credential to access the health-related information; and
   wirelessly transmitting the health-related information to the proximately located device responsive to the request received from the authenticated user and in accordance with the time-limited consent,
   wherein the portion of the health-related information is selected for transfer to the proximately located device using a filter that is based on rules established on the portable computing device by the authenticated user.

14. The method of claim 13, further comprising:
   establishing a connection through a wireless network with a plurality of electronic health records systems (EHR systems); and
   using the time-limited consent and the health-related information stored in the portable computing device to update one or more of the EHR systems.

15. The method of claim 13, further comprising:
   establishing a connection through a wireless network with a repository of electronic health records; and
   using the time-limited consent to update the repository based on the health-related information stored in the portable computing device,
   wherein the repository comprises a payor or electronic health records system.

16. The method of claim 15, further comprising:
   creating new healthcare records in a set of electronic healthcare records stored in the portable computing device; and
   using the time-limited consent to provide the new healthcare records to the repository.

17. The method of claim 16, further comprising:
   creating the new healthcare records by accessing records created by one or more applications executed on the portable computing device.

18. The method of claim 16, further comprising:
   creating the new healthcare records after receiving modified electronic healthcare records from a system operated by a healthcare provider.

19. The method of claim 18, further comprising:
   receiving modified electronic healthcare records; and
   transmitting the modified electronic healthcare records to the system operated by a healthcare provider, wherein the modified electronic healthcare records include new healthcare records created by one or more applications executed on the portable computing device.

20. The method of claim 13, wherein the portable computing device comprises a smart phone.

21. The method of claim 13, wherein the portable computing device comprises a tablet computer.

22. The method of claim 13, further comprising:
delivering new healthcare records to a computing device operated by a healthcare provider.

23. A non-transitory computer-readable medium that stores instructions, which when executed by a processor of a portable computing device, cause the portable computing device to:
use an electronic credential maintained in the portable computing device to authenticate a user of the portable computing device as an individual who owns health-related information stored in the portable computing device;
receive a transfer request from the authenticated user that includes a time-limited consent to release a selected portion of the health-related information to a proximately located device;
use the electronic credential to access the health-related information; and
wirelessly transmit the health-related information to the proximately located device responsive to the request received from the authenticated user and in accordance with the time-limited consent,
wherein the portion of the health-related information is selected for transfer to the proximately located device using a filter that is based on rules established on the portable computing device by the authenticated user.

24. The non-transitory computer-readable medium of claim 23, wherein the instructions cause the portable computing device to:
receive new healthcare records created by an application executed on the portable computing device; and
transferring the new healthcare records to a repository or to a system operated by a healthcare provider.

25. The non-transitory computer-readable medium of claim 24, wherein the instructions cause the portable computing device to:
periodically establish communication between the portable computing device and the repository or the system operated by the healthcare provider; and
transfer the new healthcare records to the repository or the system operated by the healthcare provider after communication has been established.

\* \* \* \* \*